(12) United States Patent
Kronenthal

(10) Patent No.: US 7,989,000 B2
(45) Date of Patent: Aug. 2, 2011

(54) ABSORBABLE PUTTY-LIKE IMPLANTS AND METHODS FOR THEIR USE FOR MECHANICAL HEMOSTASIS OF BONE AND FOR THE TREATMENT OF OSSEOUS DEFECTS

(75) Inventor: Richard L. Kronenthal, Fair Lawn, NJ (US)

(73) Assignee: Orthocon, Inc., Irvington, NY (US)

( * ) Notice: Subject to any disclaimer, the term of this patent is extended or adjusted under 35 U.S.C. 154(b) by 1148 days.

(21) Appl. No.: 10/941,889

(22) Filed: Sep. 16, 2004

(65) Prior Publication Data
US 2006/0002976 A1 Jan. 5, 2006

Related U.S. Application Data

(60) Provisional application No. 60/504,979, filed on Sep. 23, 2003.

(51) Int. Cl.
A61F 2/00 (2006.01)
A61K 9/14 (2006.01)
(52) U.S. Cl. .................. 424/484; 424/426; 424/489
(58) Field of Classification Search .................. None
See application file for complete search history.

(56) References Cited

U.S. PATENT DOCUMENTS

| | | | |
|---|---|---|---|
| 2,611,706 A * | 9/1952 | Bernhart et al. .............. 426/72 |
| 3,924,000 A | 12/1975 | Thiele et al. |
| 4,186,448 A | 2/1980 | Brekke |
| 4,439,420 A | 3/1984 | Mattei et al. |
| 4,443,430 A | 4/1984 | Mattei et al. |
| 4,568,536 A | 2/1986 | Kronenthal et al. |
| 4,588,583 A | 5/1986 | Pietsch et al. |
| 4,650,665 A | 3/1987 | Kronenthal et al. |
| 4,770,803 A | 9/1988 | Forseberg |
| 5,047,166 A | 9/1991 | Weil |
| 5,073,373 A | 12/1991 | O'Leary et al. |
| 5,143,730 A | 9/1992 | Fues et al. |
| 5,284,655 A | 2/1994 | Bogdansky et al. |
| 5,290,558 A | 3/1994 | O'Leary et al. |
| 5,314,476 A | 5/1994 | Prewett et al. |
| 5,356,629 A * | 10/1994 | Sander et al. ............... 424/422 |
| 5,484,601 A | 1/1996 | O'Leary et al. |
| 5,496,819 A | 3/1996 | Okuyama et al. |
| 5,641,502 A | 6/1997 | Skalla et al. |
| 5,681,873 A | 10/1997 | Norton et al. |
| 5,696,101 A | 12/1997 | Wu et al. |
| 6,030,635 A | 2/2000 | Gertzman et al. |
| 6,117,444 A | 9/2000 | Orgill et al. |
| 6,139,872 A * | 10/2000 | Walsh .......................... 424/464 |
| 6,174,422 B1 | 1/2001 | Honig et al. |
| 6,331,313 B1 | 12/2001 | Wong et al. |
| 6,413,539 B1 | 7/2002 | Shalaby |
| 6,420,454 B1 | 7/2002 | Wenz et al. |
| 6,437,018 B1 | 8/2002 | Gertzman et al. |
| 6,454,787 B1 | 9/2002 | Maddalo et al. |
| 6,485,749 B1 | 11/2002 | Shalaby |
| 6,565,884 B2 * | 5/2003 | Nimni .......................... 424/484 |
| 6,576,249 B1 | 6/2003 | Gendler et al. |
| 6,960,346 B2 | 11/2005 | Shukla et al. |
| 2002/0048551 A1 * | 4/2002 | Keller et al. ..................... 424/43 |
| 2002/0090398 A1 | 7/2002 | Dunn et al. |
| 2003/0008011 A1 * | 1/2003 | Mershon ....................... 424/487 |
| 2003/0049326 A1 | 3/2003 | Nimni |
| 2003/0093157 A1 | 5/2003 | Casares et al. |
| 2004/0018238 A1 | 1/2004 | Shukla |
| 2004/0109893 A1 | 6/2004 | Chen et al. |
| 2005/0037088 A1 * | 2/2005 | Pendharkar et al. ........... 424/490 |
| 2005/0065214 A1 | 3/2005 | Kronenthal |
| 2005/0113341 A1 | 5/2005 | Timmer et al. |
| 2005/0153869 A1 | 7/2005 | Connor et al. |
| 2006/0013857 A1 | 1/2006 | Kronenthal |
| 2006/0280801 A1 | 12/2006 | Kronenthal |

FOREIGN PATENT DOCUMENTS

| | | |
|---|---|---|
| EP | 0537559 | 4/1993 |
| GB | 1584080 | 2/1981 |
| WO | WO 95/022360 | 8/1995 |
| WO | WO 96/39995 | 12/1996 |
| WO | 00/45867 A1 | 8/2000 |
| WO | WO 01/76649 | 10/2001 |
| WO | 2005/034726 A2 | 4/2005 |
| WO | 2007/014210 A2 | 2/2007 |
| WO | 2005/034726 A3 | 5/2007 |
| WO | 2007/014210 A3 | 10/2007 |

OTHER PUBLICATIONS

Technical Bulletin Pluronic® F68 2004.*
Technical Bulletin Pluronic® L35 2004.*
Technical Bulletin Pluronic® L121 2004.*
Wang et al. Neurosurgery 2001 49:962-968.*
Rodriguez et al. "Toxicology of Polyalkylene Block Copolymers." Nonionic Surfactants. Nace ed. New York : Marcel Dekker, Inc. 1996 p. 228-229.*
Jain et al. Clinica Chimica Acta 1994 224:97-103.*
International Preliminary Report, Application No. PCT/US2006/028823, Date of Issuance: Jan. 29, 2008.
International Preliminary Report, Application No. PCT/US2004/026738, Date of Issuance: Apr. 3, 2007.
Supplementary European Search Report, Application No. EP04781435.5, Mail Date: Jul. 17, 2009.
Examination Report, Application No. EP04781435.5, Mail Date: Nov. 24, 2009.
Murohara, T., et al., Inhibition of platelet adherence to mononuclear cells by α-Tocopherol of P-Selectin. Circulation 141-148 (2004).
Onodera, S. et al. Macrophage migration inhibitory factor induces phagocytosis of foreign particles by macrophages in autocrine and paracrine fashion. Immunology 92:131-137 (1997).
Steiner, M. et al., Vitamin E: An inhibitor of the platelet release reaction. J. Clin. Inv. 57:732-737 (1976).
Tang, L. et al., Natural responses to unnatural materials: A molecular mechanism for foreign body reactions. Molecular Medicine 5:351-358 (1999).

* cited by examiner

*Primary Examiner* — Robert A Wax
*Assistant Examiner* — Caralynne Helm
(74) *Attorney, Agent, or Firm* — Ivor R. Elrifi; Muriel M. Liberto; Mintz, Levin, Cohn, Ferris, Glovsky and Popeo, P.C.

(57) ABSTRACT

Disclosed are body-implantable, appropriately absorbable, biocompatible, putty-like compositions useful as mechanical hemostatic tamponades for the control of osseous hemorrhage arising from surgical intervention or trauma and for providing an osteoinductive matrix to foster improved bone healing.

22 Claims, No Drawings

ABSORBABLE PUTTY-LIKE IMPLANTS AND METHODS FOR THEIR USE FOR MECHANICAL HEMOSTASIS OF BONE AND FOR THE TREATMENT OF OSSEOUS DEFECTS

CROSS REFERENCE TO RELATED APPLICATIONS

This application claims priority from U.S. Provisional Application No. 60/504,979 filed Sep. 23, 2003

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))

(Not Applicable)

BACKGROUND OF THE INVENTION

1. Field of the Invention

The invention relates to the surgical control of osseous hemorrhage, to the improvement of healing of osseous defects, as well as infection treatment or prophylaxis, involving orthopedic procedures utilizing materials having a putty-like consistency. More particularly, various novel, surgically implantable, absorbable, putty-like formulations, which may contain absorption accelerants, demineralized bone matrix (DBM), which is a bone growth-inducing material, and anti-infective agents to reduce the risk of postoperative infection, are used as bone hemostatic devices.

2. Description of Related Art

Cancellous and cortical bone contains relatively vascular tissues that bleed when their vasculature is disrupted. Thus, when bone is surgically incised or fractured traumatically, e.g., in open or compound fractures, there are at least two major issues which must be medically resolved. The first of these is the occurrence of osseous hemorrhage. When osseous hemorrhage ensues, it must be stopped or effectively controlled (hemostasis) to prevent adverse surgical consequences. The second issue is that of bone growth to promote healing (osteogenesis) of the traumatized bone. Common procedures in which bone is surgically cut include open-heart surgery involving the splitting of the sternum, orthopedic and spinal surgery including hip implants, neurosurgery involving spine or cranial incisions, amputations, trauma treatment, and many other procedures.

At the present time, bone hemostasis is achieved by one or more of (i) manually impregnating the bleeding surface with commercially available, non-absorbable "bone wax", (ii) the use of various hemostatic agents such as oxidized cellulose or microcrystalline collagen and (iii) electrocautery. None of these techniques promotes osteogenesis to any significant extent. In addition to the unmet need for an effective, rapidly absorbable bone hemostatic material, there is also a surgical need for materials to fill bone defect voids and promote healing in such cavities. A variety of paste-like materials, presently available to the surgeon for this purpose, most commonly are based upon coarsely powdered, demineralized allogeneic bone, suspended in a suitable, biocompatible vehicle. These compositions are designed for inducing osteogenesis and healing in the defect but, because their consistency, low cohesive strength, and other physical attributes of their composition, they do not reliably adhere to injured bone and are not effective hemostatic agents.

There are two major bodies of prior art concerned with bone hemostasis and with bone healing, respectively. As discussed below, up to the present time, in the main, only products based upon plasticized non-absorbable waxes have been available to the surgeon for bone hemostasis. The disadvantages of makeshift devices employing, for example, oxidized cellulose as well as the tissue-destructive use of electrocautery (discussed below) are not satisfactory alternatives.

The first body of art is directed specifically to bone waxes which are manually pressed into the pores of the bleeding bone surface, act as an effective mechanical tamponade, and prevent blood from escaping. Presently available bone waxes consist of mixtures of non-absorbable components such as bee's wax, paraffin, petrolatum, fatty ester plasticizers, and the like. These products must be warmed before use and become soft, kneadable and spreadable by the surgeon onto and into cut bone surfaces. Because available bone waxes are not absorbable and reside indefinitely where they are placed by the surgeon, they act as permanent physical barriers that inhibit osteogenesis, thereby preventing or slowing bone healing. In addition, such a site acts as a perpetual postoperative nidus for infection. If such infection does occur, it is usually chronic and difficult to treat using conventional anti-infective therapy and re-operation, to surgically excise the infected site, often becomes necessary. For these reasons, commercially available bone waxes do not enjoy widespread orthopedic use.

Other products or techniques used in this application include oxidized cellulose products indicated for soft tissue hemostasis, e.g., Surgicel®, which are absorbable and would not be expected to induce the complications cited above for bone wax. However, they are not effective hemostatic products for bone because of their inappropriate physical form (knitted fabric) and are too difficult to use effectively on cut bone because of lack of adherence within the bone pores.

The use of electrocautery, which thermally sears oozing blood vessels closed, is time-consuming and produces widespread tissue damage which may delay osteogenesis as well as allow soft tissue in-growth that interferes with normal bone union, presenting difficult problems for orthopedic surgeons in general and spine surgeons in particular.

Collagen and gelatin in various forms, alone or in combination with fibrin and suspended in various delivery vehicles have been proposed as bone hemostatic agents but problems with, for example, one or more of storage stability, cohesiveness, excessive swellability, and biocompatibility have prevented practical fruition.

The adaptation of synthetic absorbable polymers to this application has not succeeded, apparently because of technical difficulties in suitably formulating hydrolytically unstable synthetic absorbable polymers into practical products with reasonable package shelf life, useful handling properties and acceptable biocompatibility and absorption rates.

The second body of prior art primarily is concerned with bone healing and the treatment of bone defects. The bone healing prior art compilation primarily describes the development of biocompatible, absorbable vehicles to deliver and support processed particulate allogeneic bone as it is applied to defects such as excised bone cavities. These liquid or paste-like vehicles consist of a variety of polyhydroxy compounds, ester derivatives of polyols, hydrogels, and the like, sometimes containing additives to increase the viscosity of the vehicle (to retard dissipation of the vehicle and, thereby, extend the cohesiveness of the implanted mass) or factors to induce new bone growth. Anti-infective, anti-tumor and other additives also are described for these products. In no case, are these compositions indicated for, act as, or described in the art and claimed as bone hemostatic agents.

A. Bone Hemostasis

Attempts at providing absorbable bone hemostatic agents have not been completely successful. An absorbable bone sealant comprising fibrin and collagen (British Patent 1,584,080) requires mixing in the operating room. A reportedly hemostatic dispersion of microfibrillar collagen in polyethylene glycol (U.S. Pat. No. 6,117,444) loses coherence too rapidly as the glycol is dissipated. A microcrystalline collagen lyophilized sponge (U.S. Pat. No. 6,454,787), designed for soft tissue hemostasis, is not as well-suited for bone bleeding control. A hemostatic agent employing polylactide (U.S. Pat. No. 4,186,448), lactide/glycolide oligomers (U.S. Pat. Nos. 5,143,730, 6,420,454), moldable polymer blends (U.S. 5,641,502), absorbable, hydrogel-forming synthetics (U.S. Pat. No. 6,413,539) are not easily adapted to bone hemostasis. Polydioxanone (U.S. Pat. No. 4,443,430) synthetic absorbable polymer materials are difficult to employ because of their relative instability in biocompatible, protonic delivery vehicles. Another absorbable polyester such as a caprolactone polymer (U.S. Pat. No. 6,485,749) has been described as a replacement for bone wax.

A system with putty-like consistency at room temperature (U.S. Pat. No. 4,568,536), preferably combining a fatty acid salt, e.g., calcium stearate, an absorption enhancer, e.g., dextran and a vehicle, e.g., castor oil was developed as an absorbable, biocompatible matrix for the delivery of antibiotics, e.g., meclocycline sulfosalicylate, and other pharmacologically active agents to treat periodontal diseases. However, this technology, together with similar absorbable compositions described in U.S. Pat. No. 4,439,420 and U.S. Pat. No. 4,650,665, are deficient because they are designed for drug delivery over extended absorption time periods not thought optimal for rapid bone healing and because they contain dextran, a polysaccharide presently believed to be a toxicologically unacceptable implant material.

B. Bone Defect Healing

Materials designed for bone defect healing (but not hemostasis) are based upon pulverized cortical and/or cancellous allogeneic, demineralized, osteogenic bone powder, having particle sizes usually between 1 and 12 mm, in a biocompatible carrier selected from the group consisting of polyols, e.g., glycerol and polyol derivatives, e.g., glycerol monoacetate (U.S. Pat. No. 5,073,373, U.S. Pat. No. 5,484,601). Many additives are cited for this composition, e.g., anti-infective and anti-tumor agents, surfactants, vitamins, endocrine tissue, etc. A variant of this technology (U.S. Pat. No. 5,284,655) requires an increase of at least 10% in the volume of the demineralized bone component after contact with a swelling agent. The biocompatible suspending agent for the swollen demineralized bone particles is selected from the group including polyols and their esters, sucrose, polysaccharides, alginic acid, amylose, agar, etc. A further aspect of the 5,073,373 patent (U.S. Pat. No. 5,290,558) provides a flowable powder and claims large numbers of natural and synthetic polyols and their ester derivatives as vehicles for demineralized bone powder with a variety of additives such as BMP, IGF-1, anti-infective agents, hydroxyapatite, surfactants, bioerodable polymers and a variety of thickening agents such as PVA, PVP, CMC, gelatin, dextran, collagen, polyacrylate salts, etc. To improve handling characteristics of bone defect fillers (U.S. Pat. No. 5,314,476), particularly implant cohesion after the suspending vehicle is dissipated, demineralized bone particles of relatively high (10:1) median length to median thickness ratios are suspended in vehicles cited in the '558 patent. In an entirely different approach (U.S. Pat. No. 6,030,635), powdered demineralized bone carriers, based upon aqueous solutions of polyelectrolytes such as sodium hyaluronate, chitosan and N,O-carboxymethyl chitosan, are claimed. These viscous, high molecular weight hydrogels may contain anti-infective and other additives. A variant of U.S. Pat. No. 6,030,635 (U.S. Pat. No. 6,437,018) includes the addition of a sodium phosphate buffer to form a more viscous hydrogel carrier for smaller particle sizes of mineralized or demineralized bone.

A recently issued patent (U.S. Pat. No. 6,565,884) describes a composition based on suspended demineralized bone matrix in lecithin or in lecithin containing unsaturated triglycerides, e.g. corn oil. The product is said to induce bone growth. However, it is probable that the surface-active composition may easily be washed away after implantation. In yet another attempt to provide a useful material to stimulate new bone formation (U.S. Pat. No. 6,576,249), methods are described in which demineralized bone matrix is dissolved in water to form a viscous solution to which is added mineralized or demineralized bone matrix particles that form a water soluble, gel-like suspension.

As mentioned previously, in a search for a system to act as a matrix for the controlled delivery of various drugs, primarily for the treatment of periodontal diseases, workers developed absorbable, biocompatible, putty-like compositions that adhered to bone (teeth), were conformable at room temperature and easily applied (U.S. Pat. No. 4,568,536). While the primary objective of this composition was for prolonged drug delivery, the system was based largely upon earlier disclosed putty-like compositions specifically developed as bone hemostatic agents (U.S. Pat. No. 4,439,420).

The compositions described in U.S. Pat. No. 4,439,420 are based essentially upon combinations of three types of materials, a fatty acid salt, preferably calcium stearate, a fluid base, preferably castor oil, and an absorption accelerator, preferably dextran. This preferred composition, when tested for absorbability as an intramuscular implant, was described as taking approximately four weeks to absorb. No information or data concerning efficacy as a hemostatic device were presented and apparently no experiments were done to determine the absorption rate of the material when actually used as a bone hemostatic device. Absorption from the enclosed interstices of bone trabeculae would be expected to be significantly slower than absorption from the more anatomically "open" intramuscular site used as a model.

The 4,439,420 patent discloses alternatives for the three preferred ingredients. Alternatives to calcium stearate are magnesium, zinc, aluminum, lithium and barium salts of saturated and unsaturated fatty acids containing from 10 to 22 carbon atoms (collectively, fatty acid salts). Alternatives to castor oil are ethylene oxide/propylene oxide block copolymers, polyethylene glycols, methoxy polyethylene glycols, triglycerides, fatty acid esters, sesame oil, almond oil, cottonseed oil, corn oil, olive oil, cod liver oil, safflower oil and soya oil (collectively molecules which, admixed with the fatty acid salt, form the slowly absorbable putty-like mass). Alternatives to dextran are Carbowax®, the Pluronics®, glycerine and propylene glycol, which act as absorption accelerators by post-operatively absorbing fluids and/or dissipating, thereby physically disrupting the implant mass as it resides in tissue.

The primary reasons the 4,439,420 putty-like compositions are unsuited for bone hemostasis are that the material, while eventually biodegradable, is absorbed much too slowly and, thus, inhibits new bone growth infiltration and healing by acting as a physical barrier, much as do the nonabsorbable, paraffin-based bone waxes. In addition, the preferred composition described in the patent contains a component, i.e., dextran, which is not acceptable toxicologically. Finally, 4,439,420 compositions are "completely free of fibrous materials" which may be a significant disadvantage for optimum osteogenesis, a desirable characteristic for a bone hemostatic device. The addition of agents such as demineralized bone, bone growth factors and fibrous collagen to enhance osteogenesis and healing and anti-infectives to inhibit infection are not disclosed in the 4,439,420 patent.

BRIEF SUMMARY OF THE INVENTION

The present invention contemplates certain compositions and methods of using these compositions, as hereafter described, as mechanical hemostatic tamponades to control or to stop the bleeding of a cut or traumatized bone. The methods of the invention comprise applying the disclosed putty-like compositions, in an effective amount, to the bleeding surface of bone.

In addition, the invention includes methods for treating osseous defects by applying to the bone defect said putty-like compositions additionally containing demineralized bone matrix in a bone growth-inducing amount.

Thus, the invention provides implantable, appropriately absorbable, biocompatible, putty-like compositions that are useful as hemostatic tamponades for the control of osseous hemorrhage arising from surgical intervention or trauma and for providing an osteoinductive matrix to foster improved bone healing.

The compositions employed in the novel method of the invention are putty or putty-like in consistency. The term "putty" is used herein as it is used in the art and is generally known to the skilled artisan. Dough (such as pastry dough), modeling clay, and glazier's putty of varying viscosities, depending on the indications and ultimate use, are examples of the consistency of a suitable product. The various formulations most useable and preferable in the methods of the invention are those putties that are capable of adhering to the bone to which they are applied. In general, the putties of the invention are soft, moldable, preferably non-elastic, cohesive mixtures prepared from a carboxylic acid salt intimately admixed with a liquid dispersing vehicle and having a shape which is capable of being deformed in any direction.

The present invention involves formation of medically useful absorbable putty-like compositions using dispersing vehicles not previously reported for preparing such putty-like materials, intimately admixed with carboxylic acid salt bulking agents, some of which have been previously used, but not with the present dispersing vehicles. The compositions of the present invention are tamponades which are mechanically hemostatic (as opposed to chemically hemostatic) and in some embodiments, additionally possess osteogenic properties.

A sterile, absorbable mechanical hemostatic agent, that is, a material that will provide virtually immediate surgical mechanical hemostasis and also will absorb in the body after a relatively short period of time without compromising hemostasis efficacy, would have significant medical advantages over presently available materials. It would minimally inhibit osteogenesis and subsequent bone healing. Furthermore, adding demineralized bone matrix (DBM) to the hemostatic composition adds an osteogenic property. The addition of a suitable anti-infective agent such as tobramycin or gentamicin or anti-microbial agents such as iodine, colloidal silver, sulfadiazaine and the like, serves to reduce the potential for infection, particularly in contaminated open wounds such as compound fractures. The addition of colorants would aid in visibility during the operative procedure.

The novel and inventive concepts described below for the preparation of the products of the present invention, as illustrated in one embodiment, include at least two components, Component 1, a carboxylic acid salt, as a bulking agent and Component 2, a dispersing vehicle, which, when intimately admixed with the bulking agent in appropriate proportions, yields the putty-like products. The selection of a suitable Component 2 will result in a composition that is absorbed by the body within an acceptable period of time. In such a case, Component 2 will act as its own absorption accelerant and the formulation will not require a separate absorption accelerant. If desired, however, the compositions of the invention also may be provided with an optional ingredient which serves to accelerate the absorption of the putty by the body. Thus, in one embodiment, the composition of the invention comprises an intimate admixture of Component 1 and Component 2, with or without an added absorption accelerator, in amounts sufficient to form a putty-like consistency.

Accordingly, one aspect of the invention provides sterilizable putty-like compositions of matter and methods for their use comprising the step of physically pressing the putty-like compositions into the bleeding area of bone, thus mechanically staunching bleeding, after which the composition postoperatively is absorbed and harmlessly eliminated from the body.

In another embodiment, the compositions of the present invention comprise an intimate admixture of Component 1, Component 2, and an anti-infective agent in amounts sufficient to form a putty-like consistency. This embodiment is particularly useful in, but not necessarily limited to, traumatically opened wounds wherein the presence of an anti-infective agent inhibits the occurrence of postoperative infection.

In another embodiment, the invention comprises utilizing an intimate admixture of Component 1 and Component 2 and demineralized bone matrix (DBM) particles (Component 3) in amounts sufficient to form a putty-like consistency. This embodiment serves the dual purpose of providing initial mechanical hemostasis and stimulating new bone formation when applied to bleeding bone.

In another embodiment, the compositions of the invention comprise an intimate admixture of Component 1, Component 2, DBM in a bone growth-inducing amount, and an anti-infective agent (Component 4) in a pharmaceutically effective amount, to form a putty-like consistency.

The compositions of the invention may also include, as optional ingredients, an absorption accelerator (Component 5), a colorant (Component 6), and water.

Additional objects, features and advantages will be apparent in the written description that follows.

DETAILED DESCRIPTION OF THE INVENTION

The putty-like compositions of the present invention are mechanically hemostatic tamponades with or without demineralized bone matrix (DBM) and with or without an anti-infective agent. The compositions of the invention, the various formulations of which are set forth below in more detail, are preferably body absorbable. By "mechanically hemostatic tamponades" is meant that the compositions function by mechanically compressing the bleeding areas of the bone to arrest hemorrhaging, as opposed to functioning by chemically hemostatic means, which arrest hemorrhaging, in whole or in part, using a chemical means.

The compositions of the invention have two basic components of which Component 1 is a carboxylic acid salt bulking material having an average particle size sufficiently small to form a putty-like consistency when intimately admixed with the second component, Component 2, a dispersing vehicle. Component 1, i.e. the carboxylic acid salts, are preferably fatty acid salts such as calcium stearate or a homolog thereof such as calcium laurate. The Component 2 dispersing vehicle is preferably a liquid, which when intimately admixed with Component 1 enables the formation of the putty-like implant. These mechanically hemostatic tamponades are useful in stopping the bleeding of bone by the application of the putty-like composition to the bleeding area. In addition to being mechanically hemostatic, the compositions are also osteogenic when they contain demineralized bone matrix (DBM) to aid in the induction of bone growth as an added, but optional, ingredient. To both the basic two-Component hemostatic compositions and the composition comprising the DBM, may be added an anti-infective agent to provide infection control.

As a statement of general applicability, in the discussion which follows of the materials useful in the compositions of the present invention, unless specifically indicated otherwise, organic carbon atom chains may be straight chains or branched chains.

Component 1

Component 1 is comprised of a finely powdered, compatible, body-absorbable carboxylic acid salt which, when admixed with a liquid dispersing vehicle, Component 2, forms the putty-like compositions of the invention. Suitable results are obtained when the average particle sizes of Component 1 materials are about 50 microns or less, but the preferred average particle size range is between about 3 to about 25 microns and most preferably about 6 to about 15 microns.

Examples of one set of materials suitable for use herein are salts of one or more carboxylic acids having a carboxylate anion and a metal cation, some which are known in the art, having been described in U.S. Pat. Nos. 4,439,420 and 4,568,536. Suitably, the salts may be the calcium, magnesium, zinc, aluminum, lithium or barium salts of saturated or unsaturated carboxylic acids containing about 6 to 22 carbon atoms in the chain and preferably 8 to 20 carbon atoms. The preferred saturated carboxylic acids supplying the carboxylate anion may be selected from aliphatic acids such as caprylic acid, capric acid, lauric acid, myristic acid, palmitic acid, stearic acid, arachidic acid, and intervening homologs thereof, but the most preferred acids are the higher fatty acids such as lauric, myristic, palmitic, and stearic acids, with stearic being most preferred. Calcium and aluminum palmitates and stearates are preferred salts with calcium stearate being most preferred because of its excellent safety profile, and putty-forming characteristics. However, aluminum stearate, aluminum palmitate, or aluminum laurate, are suitable as well. Examples of suitable unsaturated aliphatic acids which may be used for supplying the carboxylate cation are oleic acid and linoleic acid for which the same cations described above are used.

Component 2

As the second component, i.e., the material which is mixed with Component 1 to obtain the bone putties of the invention, there may be mentioned several classes of materials that have not heretofore been employed as dispersing vehicles for preparing medical putties. At the outset, it should be noted that Component 2 is biocompatible and preferably a liquid because the liquid form facilitates the admixture with Component 1 to form the putty mass. It will be appreciated, however, that Component 2 may also be a solid if a liquid vehicle (a liquefying agent, as more fully discussed below) is used to act as a medium for Components 1 and 2.

To aid in understanding the terms used herein and to help differentiate this aspect of the invention from that of the prior art, it would, perhaps, at this point, be useful to emphasize the nature of the chemical entities referred to in this Specification by briefly reviewing relevant classical chemistry terminology to ensure the appropriate chemical distinctions are understood.

Carboxylic acids are substances defined by the attachment of an OH group to a carbonyl function through a covalent bond. As a result, carboxylic acids possess physical and chemical properties totally distinct from substances containing either the carbonyl functionality (e.g., aldehydes, ketones) or the hydroxyl functionality (alcohols). The same distinction holds true for substances containing both the carbonyl and hydroxyl groups not directly attached through a covalent bond, such as hydroxyacetone, which displays both ketone and alcohol properties, but not carboxylic acid characteristics. Carboxylic acids always combine a carbonyl and an OH group and have acidic characteristics, but the OH group does not have the characteristics of the hydroxyl group of an alcohol. A monocarboxylic acid would, therefore, not be described as a monohydroxy compound. To illustrate this, consider acetic acid and ethanol which are both two-carbon compounds containing an OH group. In acetic acid, the hydrogen atom of the OH group is liberated as an ion in water, whereas in ethanol, the hydrogen atom of the hydroxyl group is not so liberated. Thus, carboxylic acids dissociate and form carboxylate salts with bases, e.g., calcium stearate, a distinctive property that clearly differentiates the OH group of carboxylic acids from the hydroxyl group of alcohols that do not dissociate to form salts with bases. Thus, it would be entirely incorrect to characterize a carboxylic acid as an alcohol, a monohydric alcohol, or some such term since it is, in no chemical sense, an alcohol. Nor could a polycarboxylic acid be referred to as a polyalcohol, or a polyhydroxy compound or a polyol simply because it contains carboxylic OH groups. Such groups are not characterized as alcohols. An example of these distinctions is illustrated by considering the well-known molecule, citric acid. This substance has three carboxylic groups and one hydroxyl group in the same molecule. Citric acid is a monohydroxy (monohydric) alcohol as well as a polycarboxylic acid. The fact that citric acid contains three carboxylic OH groups does not classify this monohydroxy compound as a polyhydroxy compound. Because of the major differences in reactivity, synthesis and reactions, in every textbook of organic chemistry, the chemistry of alcohols always is considered in a separate chapter from the chemistry of carboxylic acids.

Alcohols may be regarded either as hydroxyl derivatives of hydrocarbons or as alkyl derivatives of water. They are typified by the R—OH structure where R is an alkyl group. In contradistinction to the readily ionizable hydrogen atom of the carboxylic acid hydroxyl group, the R—OH hydrogen atom is virtually unionized in water. On this basis, aliphatic alcohols are considered neutral rather than acidic. One or more hydroxyl groups may be appended to a hydrocarbon moiety so that, for example, propane may have one hydroxyl group (propyl alcohol), two hydroxyl groups (propanediol or propylene glycol) or three hydroxyl groups (propanetriol or glycerol). Propylene glycol and glycerol are simple examples of polyols. Polysaccharides, such as hyaluronic acid, contain many hydroxyl groups on each monomer unit and are correctly termed polyols. Alcohols may have short alkyl chains such as methyl alcohol, ethyl alcohol, propyl alcohol, etc., or they may have longer alkyl chains such as lauryl alcohol, myristyl alcohol, etc. It is of critical importance to note that lauric acid ($C_{11}H_{23}COOH$, a fatty acid) and lauryl alcohol ($C_{12}H_{25}OH$, a fatty alcohol) are completely different molecules in oxidation state, functionality, and reactivity, even though they both contain twelve carbon atoms.

Esters commonly are derived from the reaction of a carboxylic acid with an alcohol and can be converted back to the original carboxylic acid and alcohol by hydrolysis. Thus, acetic acid and ethyl alcohol are combined in the esterification process to form ethyl acetate and water. The term fat (or vegetable or animal oil) is confined to esters of a variety of long chain saturated or unsaturated fatty acids with glycerine (glycerides). Oils, cited in the prior art as vehicles for preparing putty-like materials, are exclusively glycerides, e.g., castor oil, sesame oil, olive oil, etc., as well as simple fatty acid esters such as ethyl laurate. What never have been proposed in the prior art as vehicles for preparing putty-like substances, are free liquid fatty carboxylic acids such as the saturated caprylic acid and the unsaturated oleic acid. Most important, the use of esters of fatty alcohols with low molecular weight mono- or polycarboxylic acids, e.g., lauryl acetate (the ester of lauryl alcohol and acetic acid) are completely novel for the preparation of putty-like materials and are chemically distinct from the prior art cited ethyl laurate (the ester of lauric acid with ethyl alcohol).

Returning now to the description of the Components of the present invention, more particularly Component 2, the elements are more specifically described as follows:

As a first class of Component 2, there are one or more absorbable esters of a $C_8$-$C_{18}$ monohydric alcohol with a $C_2$-$C_6$ aliphatic monocarboxylic acid. The monohydric alcohols may be selected from $C_8$-$C_{18}$ alcohols such as octyl alcohol, decyl alcohol, lauryl alcohol, myristyl alcohol, stearyl alcohol, and intervening homologs thereof. The preferred alcohols are the higher aliphatics such as lauryl alcohol, myristyl alcohol, and stearyl alcohol. Illustrative of the useful esters formed with the $C_2$-$C_6$ monocarboxylic acids are lauryl acetate and myristyl propionate.

As a second class of Component 2, there are one or more absorbable esters of a $C_2$-$C_{18}$ monohydric alcohol with a polycarboxylic acid. The $C_2$-$C_{18}$ monohydric alcohols include, in addition to the $C_8$-$C_{18}$ alcohols described in the first class of esters there are the lower aliphatic, $C_2$-$C_7$, alcohols such as ethanol, propanol, butanol, pentanol, hexanol, heptanol, and octanol which yield the ethyl, propyl, butyl, pentyl, hexyl, heptyl and octyl moieties. The polycarboxylic acids may be selected from malonic, succinic, glutaric, adipic, pimelic, suberic, azelaic, sebacic, maleic, fumaric, glutaconic, citric, malic acids, and esters of the hydroxy function, if any, of the esterified polycarboxylic acid, especially acetyl citric acid and acetyl malic acid. It will be obvious to those skilled in the art that many combinations of alcohol/acid esters may be selected from the above, but the preferred ones for use in the invention from the monohydric alcohol/polyacid esters are diethyl succinate, dioctyl succinate, triethyl citrate, tributyl citrate and higher and lower homologs thereof, acetyl triethyl citrate, acetyl tributyl citrate, butyryl triethyl citrate, and higher and lower homologs thereof, diethyl malate, di-pentyl malate, and acetyl diethyl malate, and higher and lower homologs thereof.

Another class of materials, suitable as Component 2, are the higher $C_8$-$C_{12}$ up to about $C_{30}$ and preferably liquid or liquefiable monohydric alcohols such as octanol and decanol.

An especially surprisingly suitable embodiment of this class is the aromatic alcohol tocopherol (Vitamin E) in its optically active or racemic forms, in any of the alpha, beta, gamma or delta forms, as well as liquid tocopherol esters (sometimes referred to herein as tocopherol esters) with a $C_2$-$C_{10}$ aliphatic monocarboxylic acid, a polycarboxylic acid or mixtures thereof. Useful are the tocopherol esters such as acetates, butyrates, caproates, caprylates, caprates, and intervening homologs thereof, and polycarboxylic acid ester such as those mentioned in the previous paragraph, especially esters of succinic, citric, and malic acids, with succinate being preferred.

Another class of materials, useful as Component 2, are absorbable hydrocarbons having from about 10-14 carbons atoms. For example, decane and dodecane are suitable.

Another class of materials, useful as Component 2, are the liquid or liquefiable saturated or unsaturated, free carboxylic acids such as the non-esterfied fatty acids, oleic, linoleic, caprylic, capric, and lauric. In this class, the normally liquid, saturated fatty acids would be suitable but may not be desirable because of their unpleasant odor. Some low melting saturated free-fatty acid mixtures that form a lower-melting eutectic mixture which is liquid at room temperature may also be suitable. One advantage of saturated free-fatty acids lies in their improved stability to radiation sterilization whereas the unsaturated acids, e.g., oleic, may require radiation sterilization in an oxygen-free package. Higher homologs of solid acids can also be used in admixture with Component 1 in the presence of a liquefying medium or other suitable component. Any compatible liquid may be used as long as it ensures the liquefaction of Component 2 and is biocompatible as well.

Another class of materials, useful as Component 2, are ethers of the simple dialkyl ether class and alkyl aryl ether class as well as cyclic polymers of alkylene glycol e.g., ethylene glycol, known as crown ethers, all having boiling points greater than about 80° C. such as di-n-hexyl ether, di-n-octyl ether, and unsymmetrical ethers such as ethyl hexyl ether, ethyl phenyl ether, and the like or, block copolymers of ethylene oxide and propylene oxide in various ratios of ethylene oxide to propylene oxide and various molecular weights, preferably from 1000 to 10,000, (Pluronics®). They are available in liquid or solid form. Illustrative of suitable materials are those shown below in examples 37, 38, and 39. In addition to their suitability for use as a Component 2, they may also be used as an absorption accelerant (Component 5). They are available under the trade name, Pluronics® from BASF Corp. Mt. Olive, N.J. 07828.

Another class of materials, useful as Component 2, are symmetrical and unsymmetrical dialkyl ketones and alkyl aryl ketones having boiling points greater than about 80° C. such as methyl propyl ketone, diethyl ketone, methyl butyl ketone, ethyl propyl ketone, methyl pentyl ketone, and 2-octanone, 2-nonanone, 2-decanone, and methyl phenyl ketone.

Another class of materials useful as Component 2 are selected from a member of the group consisting of polyhydroxy compounds, polyhydroxy compound esters, solutions of polyhydroxy compound, and mixtures thereof, and fatty acid esters. Preferred among these are the liquid polyhydroxy compounds selected from the group consisting of acyclic polyhydric alcohols, polyalkylene glycols, and mixtures thereof. Specific examples of the foregoing are ethylene glycol, diethylene glycol, triethylene glycol, 1,2-propanediol, trimethylolethane, trimethylopropane, erythritol, pentaerythritol, polyethylene glycols, a liquid solution of a fatty acid monoester of glycerol such as glycerol monolaurate. Solids among the foregoing may be dissolved or dispersed in a suitable solvent medium such as propylene glycol, glycerol, monoacetin, diacetin, liquid polyethylene glycol, and mixtures thereof. It should be noted that the foregoing polyhydroxy compounds may also be used, if desired, as Component 5 absorption accelerants.

Another class of compounds useful as Component 2 are triglycerides, especially olive oil, castor oil, almond oil, sesame oil, cottonseed oil, corn oil, cod liver oil, safflower oil and soya oil.

As a statement of general applicability, it should be noted that Component 2 materials which are liquid at room temperature are the preferred substances for Component 2, and since they are liquids, a liquefying agent is not necessary. Also useful as Component 2 substances, however, are compounds which are solid at room temperature. In such cases, especially when putties are desired, a solid Component 2 is converted to a liquid form before, during, or after admixture with Component 1 through temperature. In such cases, especially when putties are desired, a solid Component 2 is converted to a liquid form before, during, or after admixture with Component 1 through the use of an absorbable biocompatible liquefying agent capable of liquefying or solubilizing a solid Component 2. By "liquefying agent", as used herein, is meant an agent, such as a suitable solvent, which can solubilize the solid, or any other agent even though the agent may not be considered a solvent in the usual sense of that term, or an agent which can liquefy the solid, such as heat, or which can disperse the solid in a liquid as a dispersion so as to aid in the formation of a homogenous putty. The particular agent used will, of course, depend upon the nature of Component 2 used in the particular formulation. Suitable agents are materials similar to Component 2 though not precisely described herein as Component 2.

The foregoing novel concepts and compositions utilizing the esters of monoalcohols with the mono- or polycarboxylic acids described above, provide an absorbable bone hemostatic implant. The novel utilization of relatively low molecular weight, non-toxic and rapidly degradable simple esters such as diethyl succinate, triethyl citrate and lauryl acetate have been found to provide superior alternatives to the much higher molecular weight fatty acid triglycerides, e.g., castor oil, for Component 2. This aspect of the invention thus permits one to eliminate, if desired, both the art-known version of Component 2, i.e. hydrophobic, slowly absorbed esters such as the triglycerides typified by the ricinoleic acid triglyceride, castor oil, as well as by fatty acid esters such as ethyl laurate and the need for the use of an absorption accelerant.

These art-known putty compositions containing the art-known Component 2 materials, such as those of U.S. Pat. No. 4,439,420 can, however, be used to obtain useful osteogenic bone hemostatic materials in accordance with another aspect of the invention. It has been discovered that, when it is desired to have a bone hemostatic composition having osteogenic properties albeit with slower absorption characteristics, the art-known composition may be improved by the addition of demineralized bone matrix (DBM).

The compositions of the invention may also, (but are not required to), contain if desired, in addition to Component 1 and Component 2, optional ingredients which include DBM, an anti-infective agent, an accelerant enhancer, a colorant, and water. It will be appreciated that such optional components need not be present, the two-component putty system of Components 1 and 2 being sufficient to provide the basic characteristics of a suitable hemostatic tamponade.

Component 3

The products described above comprising Component 1 and Component 2 are suitable hemostatic products which also will allow the growth of bone at the bone wound site. However, if it is desired to impart to the hemostatic product osteoinductive properties as well, optional Component 3, i.e. demineralized bone matrix (DBM) may be added, in an amount and particle size effective to induce bone growth.

When used, a suitable amount of DBM, to be added to the compositions of the present invention ranges from about 10% to about 60% and preferably about 10% to 50% and most preferably about 30% to about 40% by weight. It is preferred to use DBM in the form of average particle sizes in the range of about 0.05 to 10 mm, preferably about 0.1 to 5 mm and, most preferably about 0.5 to 1 mm. However, the use of Component 3 in smaller or larger particle sizes or in higher or lower amounts will also be suitable if the requirements of the ultimate user are satisfied.

The addition of the DBM improves not only the compositions of the invention, but also improves the prior art hemostatic formulations to yield novel compositions therewith. Such additions will render these hemostatic formulations osteogenic as well. It is believed that the presence of the osteogenic material will also improve osteoconductive properties because the relatively large particles tend to "open up" the putty structure, thus providing spaces into which induced bone may proliferate. the aforementioned patents were reproduced herein verbatim. For purposes of convenience, the formulations of those patents may be generally characterized as comprising an absorbable hemostatic composition for use in the control of osseous hemorrhage, comprising: a component comprising a biocompatible fatty acid salt, the cation of said fatty acid salt being selected from the group consisting of calcium, magnesium, zinc, aluminum, lithium and barium and a component comprising a body absorbable biocompatible base selected from the group consisting of ethylene oxide/proplylene oxide block copolymers, polyhydroxy compounds, polyethylene glycols and methoxypolyethylene glycols, triglycerides and fatty acid esters, and an optional absorption enhancing agent. Thus, in this aspect of the invention, the DBM is added to the above prior art formulations to produce an osteogenic hemostatic material.

Component 4

To the compositions described above may be added, as optional Component 4, a pharmaceutically effective amount of an anti-infective agent, either alone or bound to a substrate to slow its release. Illustrative of antibiotics are tetracycline, vancomycin, cephalosporins, and aminoglycosides such as tobramycin and gentamicin, alone or bound to collagen, for example, and combinations of the foregoing. Illustrative of anti-microbial agents are silver salts, colloidal silver, silver sulfadiazine, and iodine alone or employed with polyvinylpyrrolidone (PVP) termed Povidone.

Other Optional Ingredients

Another optional ingredient for the compositions of the invention is an absorption accelerant (Component 5), preferably a hydrophilic material. In some instances, it may participate in the control of the kinetics of absorption by physically assisting in the disintegration of the implanted mass. Accelerants used in the prior art may be used if they are not toxic or otherwise bioincompatible. One or a combination of such prior art compounds as Carbowax®, the Pluronics®, (See discussion under Component 2, supra and discussion below) glycerine, propylene glycol, lecithin, betaine and polyhydroxy compounds such as hyaluronic acid, carboxymethylcellulose, and chitosan and its acetyl derivatives, may be used as absorption enhancers in the compositions of the invention, with the above caveat. It is preferred, however, to use for this purpose, other materials which are swellable or soluble and absorbable, such as either soluble or insoluble, natural or synthetic polypeptides, exemplified by purified, powdered insoluble fibrillar, but swellable collagens, the more rapidly absorbable soluble tropocollagens such as Vitrogen® and the more rapidly absorbable cold and hot water soluble polypeptides, e.g. the gelatins. Lecithin and octylphenyl ethoxylates such as Triton® X 100, may be used as biocompatible surfactants to aid in swellability. Polyvinylpyrrolidone and other soluble, absorbable polymers such as the block copolymers of ethylene oxide and propylene oxide discussed supra in connection with Component 2; and relatively hydrophilic and synthetic polypeptides, e.g., polyaspartic acid, polyglutamic acid, and their salts are also functional in this context. Most preferably, the compositions of the present invention contain, as the absorption accelerant, insoluble, fibrillar collagen, soluble collagen, gelatin, lecithin, betaine, octylphenyl ethoxylates, the block copolymers of ethylene oxide and propylene oxide, polyvinylpyrrolidone or absorbable phosphorus pentoxide-based glasses or stable mixtures of the foregoing. Particle sizes in the range of about 200-500 microns produce suitable results although larger or smaller particle sizes may be employed depending on the desires of the end user. Gelatin, PVP and other polymers have been used in the demineralized bone art as thickening additives but not as absorption accelerators. The thickening properties of gelatin vary directly with the Bloom number of the gelatin. Gelatins having Bloom numbers ranging from 100-300 are suitable in the compositions of the present invention although values outside that range may be used if the resulting product is satisfactory to the end user.

The components described above, when added together in suitable proportions, yield useful, putty-like hemostatic agents having, to varying degrees, many favorable characteristics. Various combinations of the components may require different times and temperatures in the preparation process in order for the putty-like characteristics to develop. For example, some materials may take longer than other components to achieve the putty-like state. In general, the putty-like compositions of the present invention are develop. For example, some materials may take longer than other components to achieve the putty-like state. In general, the putty-like compositions of the present invention are absorbable within a reasonable time, usually within 30 days although absorption times may be extended to several months or longer for some applications. They usually are moldable and shapeable by hand at ambient temperatures, handle well in presence of blood, and are washable with saline. They sometimes are tacky to the touch, but do not stick to any great degree to surgical gloves, wet or dry. They can be radiation sterilized when radiation-sensitive material such as DBM or certain antibiotics are not present.

The actual proportions of the materials selected will vary depending upon the materials themselves, the number of components used and the use desired for the final putty composition. The user will be guided by the requirement for a putty-like consistency to be obtained while maintaining other characteristics desired in the ultimate use of the component.

Illustrative of some suitable proportions of components to produce compositions having the properties described above are the following:

Component 1. From about 5 to 80%, preferably about 20 to 50% by weight of the final composition.
Component 2. From about 10 to 70%, preferably about 20 to 50% by weight of the final composition.
Component 5. From about 0 to about 80%, preferably about 10-70% by weight of the final composition.
Colorant—Component 6
Depending upon the tinctorial power of the colorant selected, and the composition of the putty, an optional colorant such as gentian violet, D&C Violet #2, and D&C Green #6, is suitably added to the composition of the present invention.

Water—Component 7

In some embodiments of the invention, it may be desirable to intimately admix water as an optional Component (7) with the compositions of the invention. The presence of a small amount of water, of the order of up to ten percent or more, aids in a variety of ways, among which is changing the tactile quality of the composition. In this regard, the resulting compositions often impart a sensation of reduced coarseness over what may have existed in the compositions without the water addition.

The compositions described in this specification, when used surgically, must be sterile. All, except those noted below, are radiation sterilizable using, for example, a standard cobalt-60 radiation source and a nominal dose of 25 kGy. Exceptions are formulations containing radiation-sensitive additives such as demineralized bone matrix, certain antibiotics, unsaturated molecules such as oleic acid, and the like. When such materials are used, sterility may be achieved by radiation-sterilizing the bulk putty-like material and aseptically adding the pre-sterilized radiation-sensitive additive followed by aseptic packaging.

The compositions described in this specification may be packaged in several formats and may be sterile or sterilizable. The packages themselves may be sterile or sterilizable. The compositions may be packaged as an amorphous (i.e., shapeless or having no definite shape) putty, or in the shape of its container. They may be shaped generally as a parallelepiped or as a generally rounded form, examples of the former being small brick-shapes or slabs (in the shape of a stick of chewing gum), and examples of the latter being cylindrically-shaped, egg-shaped, or spherically-shaped products. Alternatively, when the application permits and the viscosity is suitable, the putty can be packaged in a syringe-like or plunger-assisted dispenser expressible or extrudable through an orifice of appropriate cross section and shape. A mechanical assist device similar to that for applying caulking may be included. Another package contains the product in a squeezable, deformable tube such as a toothpaste-type tube or a collapsible tube such as those used in caulking applications, with an orifice shaped and sized to dispense any suitable shape onto the surface to be treated. The package may comprise an outer barrier as an overwrap, for example, a peelable blister pouch, to allow aseptic delivery of the package to the sterile field.

The present invention also contemplates methods of use of the compositions of the invention. For example, one embodiment is the method of mechanically controlling the bleeding of bone by the application of an effective amount of any of the putty-like compositions of the invention to bleeding bone. In such a case, the composition is a mechanical hemostatic tamponade.

As previously indicated, the methods also include the treatment of osseous defects, especially when the compositions include DBM. That is, a method of the invention is the method for inducing bone growth in a bone defect applying an effective amount of any composition of the invention which contains DBM, to the affected area of the bone.

Another embodiment is the method for treating bleeding bone or bone defects by applying thereto the disclosed compositions wherein the compositions include an antibiotic agent. That is, the invention includes a method for treating an infection in or around bone by applying an effective amount of any composition of the invention which contains an anti-infective agent to the affected area of the bone to be treated.

Those skilled in the art will be aware of the manner in which the compositions are applied and the amount thereof. The amounts will generally vary depending upon the application and the particular needs of the patient during surgery.

The methods and examples provided below are intended to more fully describe preferred embodiments of the invention and to demonstrate its advantages and applicability.

The following examples illustrate specific embodiments of the present invention.

EXAMPLE 1

In this example and in all subsequent examples, unless otherwise indicated, the composition was prepared by mechanical blending of all dry reagents first and thereafter adding gradually any liquid reagents. The composition was "worked" with a spatula at room temperature until the desired consistency was obtained. In some cases, if the material needed additional ingredients to improve the consistency, that material was added and the mixture continually kneaded or "worked" until the desired putty-like consistency was obtained. The components are presented in parts by weight.

| | | |
|---|---|---|
| Component 1 | Calcium stearate | 4 g. |
| Component 2 | Tocopheryl acetate | 3 g. |
| Absorption Accelerant | Gelatin | 3 g. |

The sample yielded a putty-like mass with excellent water resistance, physical and hemostatic characteristics and water resistance properties, i.e., it resisted strongly attempts at washing it away under the force of flowing tap water.

EXAMPLE 2

| | | |
|---|---|---|
| Component 1 | Aluminum Palmitate | 5 g. |
| Component 2 | Tocopheryl acetate | 3 g. |
| Absorption Accelerant | Gelatin | 3 g. |

The resulting product is a putty-like mass with properties similar to those described for the product in Example 1.

EXAMPLE 3

| | | |
|---|---|---|
| Component 1 | Calcium stearate | 5 g. |
| Component 2 | Tocopheryl acetate | 3 g. |
| Component 3 | DBM | 3 g. |
| Absorption Accelerant | Gelatin | 3 g. |

The resulting product, in addition to having hemostatic properties of the product of Example 1, is osteogenic.

EXAMPLE 4

| | | 4a. | 4b. |
|---|---|---|---|
| Component 1 | Calcium stearate | 2 g. | 1.3 |
| Component 2 | Triethyl citrate | 1.6 g. | 0.98 |
| Component 3 | Triton ® X 100 | 0 | 0.02 |

The resulting product 4a, was putty-like and had physical characteristics similar to those of Example 1. Product 4b was also putty-like and is more rapidly absorbable than 4a. Triton® X 100 is available from Dow Chemical Co., Midland, Mich.

EXAMPLE 5

| | | |
|---|---|---|
| Component 1 | Calcium stearate | 4 g. |
| Component 2 | Triethyl citrate | 3 g. |
| Absorption Accelerant | Gelatin | 3 g. |

The resulting product was putty-like and had physical characteristics useful as a hemostat, but not preferred when compared to the product of Example 4.

EXAMPLE 6

| | | |
|---|---|---|
| Component 1 | Calcium stearate | 2 g. |
| Component 2 | Acetyl triethyl citrate | 2 g. |

The resulting product has excellent putty-like characteristics and physical characteristics comparable to those of Example 1.

EXAMPLE 7

| | | |
|---|---|---|
| Component 1 | Calcium stearate | 3 g. |
| Component 2 | Tocopheryl acetate | 1.0 g. |
| Component 2 | Triethyl citrate | 1.5 g. |
| Absorption Accelerant | Gelatin | 2 g. |

The resulting product was a good material with putty-like physical characteristics similar to those of Example 1 and somewhat more sticky than that of Example 1.

EXAMPLE 8

| | | |
|---|---|---|
| Component 1 | Calcium stearate | 4 g. |
| Component 2 | Lauric acid | 4 g. |
| Component 2 | Tocopheryl acetate | .5 g. |

The calcium stearate was blended with melted lauric acid and formed a good putty which upon cooling solidified. The solid was then crushed and blended with the tocopherol to yield a good putty.

EXAMPLE 9

| | | |
|---|---|---|
| Component 1 | Calcium stearate | 4 g. |
| Component 2 | Triethyl citrate | 4 g. |
| Component 2 | Lauric acid | 4 g. |

The resulting product was putty-like and had physical characteristics similar to those of Example 1 and with somewhat less cohesiveness.

EXAMPLE 10

| Component 1 | Calcium stearate | 2 g. |
|---|---|---|
| Component 2 | Dodecane | 1 g. |

The resulting product had good water resistance, was of lower viscosity and compared well with the other physical characteristics of Example 1.

EXAMPLE 11

| Component 1 | Calcium stearate | 2 g. |
|---|---|---|
| Component 2 | Octanol-1 | 1 g. |

The resulting product was of lower viscosity and had physical characteristics similar to those of Example 10 but somewhat less cohesive.

EXAMPLE 12

| Component 1 | Calcium stearate | 2 g. |
|---|---|---|
| Component 2 | Diethyl succinate | 2 g. |
| Absorption Accelerant | Gelatin | 2 g. |

The resulting product was a good putty similar to Example 1.

EXAMPLE 13

| Component 1 | Calcium stearate | 4 g. |
|---|---|---|
| Component 2 | Diethyl succinate | 3 g. |

The resulting product was a good putty which had improved consistency over that of Example 12.

EXAMPLE 14

| Component 1 | Calcium stearate | 4 g. |
|---|---|---|
| Component 2 | Acetyl triethyl citrate | 3 g. |
| Absorption Accelerant | Gelatin | 3 g. |

The resulting product was comparable to that obtained in Example 1.

EXAMPLE 15

| Component 1 | Aluminum palmitate | 4 g. |
|---|---|---|
| Component 2 | Tocopheryl acetate | .3 g. |
| Component 2 | Triethyl citrate | 3 g. |

The resulting product was a soft, somewhat translucent putty with good water resistance and good hemostatic characteristics.

EXAMPLE 16

| Component 1 | Calcium stearate | 3 g. |
|---|---|---|
| Component 2 | Tocopheryl acetate | 3 g. |
| Component 3 | Demineralized bone matrix | 1 g. |
| Absorption Accelerant | Gelatin | 3 g. |

The resulting product is a putty-like mass with properties comparable to the product in Example 1 and has osteogenic properties as well.

EXAMPLE 17

| Component 1 | Calcium stearate | 3 g. |
|---|---|---|
| Component 2 | Di-n-hexylether | 2.5 g. |
| Absorption Accelerant | Gelatin | 2 g. |

The resulting product is putty-like and has good water resistance and physical characteristics similar to those of Example 1.

EXAMPLE 18

| Component 1 | Calcium stearate | 3 g. |
|---|---|---|
| Component 2 | Di-n-pentylketone | 2.5 g. |
| Absorption Accelerant | Gelatin | 2 g. |

The resulting product is putty-like and has good water resistance and physical characteristics similar to those of Example 17.

EXAMPLE 19

| Component 1 | Calcium stearate | 3 g. |
|---|---|---|
| Component 2 | Tocopheryl acetate | 3 g. |
| Absorption Accelerant | Bovine collagen (powdered) | 3 g. |

The resulting product is putty-like, has good water resistance and physical characteristics similar to those of Example 18. In addition, the putty has a fibrous texture as a result of the fibrous powdered collagen sponge additive present as the absorption accelerant (Component 3).

EXAMPLE 20

| Component 1 | Calcium stearate | 3 g. |
| Component 2 | Tocopheryl acetate | 3 g. |
| Absorption Accelerant containing antibiotic | *Bovine collagen (powdered) containing gentamicin sulfate | 3 g. |

*Collatamp G available in Europe

There results a hemostatic putty with anti-infective properties.

EXAMPLE 21

| Component 1 | Calcium stearate | 4 g. |
| Component 2 | Tocopheryl acetate | 3 g. |
| Absorption Accelerant | Gelatin | 3 g. |
| Antibiotic | Gentamicin sulfate | 120 mg. |

Example 1 is repeated except that 120 mg. of gentamicin sulfate is combined with the dry components before the tocopheryl acetate is added to make a putty. This example demonstrates the preparation of a putty with anti-infective properties.

EXAMPLE 22

The following composition is described in U.S. Pat. No. 4,439,420 as a preferred composition of about 40% calcium stearate, 30% dextran and 30% castor oil. If water is added, the preferred composition is 38% calcium stearate, 28% dextran, 27% castor oil and 7% water (all weights are weight percent). The composition was prepared by mechanical mixing at ambient temperatures to avoid possible degradation of heat-sensitive components.

| Calcium stearate | 4 g. |
| Castor oil | 3 g. |
| Dextran | 3 g. |

The calcium stearate and dextran were dry blended in a 50 ml glass beaker and the castor oil was added with stirring using a spatula. After several minutes of "working" the mixture with the spatula at room temperature, the consistency gradually changed. The mixture became crumbly and, after further working, became putty-like.

EXAMPLE 23

The formulation in Example 22 was modified as indicated below to make a novel, putty-like composition of the present invention. The mass is an effective hemostat and is an effective osteogenic bone defect filler.

| Calcium stearate | 2 g. |
| Castor oil | 1.5 g. |
| Dextran | 1.5 g. |
| DBM (demineralized bone matrix) | 1.5 g. |

The purpose of this example is to show that DBM can be added to the compositions described in U.S. Pat. No. 4,439,420 to obtain a putty-like mass with osteogenic properties.

EXAMPLE 24

| Component 1 | Calcium stearate | 3 g. |
| Component 2 | Ethyl laurate | 3 g. |
| Component 3 | Demineralized bone matrix | 1 g. |

The purpose of this example is to show that DBM can be added to the compositions described in U.S. Pat. No. 4,439,420 to obtain a putty-like mass with osteogenic properties.

EXAMPLE 25

| Component 1 | Calcium Stearate | 1 g. |
| Component 2 | Tocopheryl acetate | 1 g. |
| Component 2 | Glycerol | .25 g. |

There resulted a relatively soft putty with excellent water resistance.

EXAMPLE 26

| d,l-alpha tocopheryl acetate | 1.6 g. |
| calcium stearate | 0.6 g. |
| potato starch* | 3.8 g. |

*Razin International, Inc.
6527 Route 9
Howell, New Jersey 07731

The tocopheryl acetate and calcium stearate were mixed together and the starch was then added. The mixture formed a soft, white putty with good water resistance. To prevent the formation of post-operative adhesions, it may be desirable to sterilize the putty using 25 kGy of ionizing gamma radiation from a cobalt 60 source in order to degrade the starch. Alternatively, the starch may be subjected to radiation degradation prior to formulating it into the putty.

The following examples 27-33 show putty compositions, prepared as in Example 1, having good water resistance and incrementally increasing absorbabilities from slowly absorbable to more rapidly absorbable as the amount of gelatin is increased relative to the amount of calcium salt.

|  | Parts Ca salt | Parts component 2 | Parts- | gelatin- % |
| --- | --- | --- | --- | --- |
| EXAMPLE 27 | 12 Ca stearate | 7.5 tocopheryl acetate | 0 | 0 |
| EXAMPLE 28 | 12 Ca stearate | 7.5 tocopheryl acetate | 2.0 | 10 |
| EXAMPLE 29 | 12 Ca stearate | 7.5 tocopheryl acetate | 3.5 | 15 |
| EXAMPLE 30 | 12 Ca stearate | 7.5 tocopheryl acetate | 5.0 | 20 |
| EXAMPLE 31 | 12 Ca laurate | 7.5 tocopheryl acetate | 4.5 | 20 |
| EXAMPLE 32 | 12 Ca laurate | 7.5 tocopheryl acetate | 4.5 | 20 |
| EXAMPLE 33 | 0.6 Ca stearate | 1.6 tocopheryl acetate | 5.0 | 70 |

EXAMPLE 34

| Component 1 | Ca stearate | 3.4 |
|---|---|---|
| Component 2 | tocopheryl acetate | 3.2 |
| Absorption Accelerant | Gelatin | 4.4 |

The resulting product has characteristics similar to the putty of Example 1.

EXAMPLE 35

| Component 1 | Ca stearate | 3.0 g |
|---|---|---|
| Component 2 | tocopheryl acetate | 0.4 g |
| Component 2 | tributyl citrate | 2.3 g |
| Absorption Accelerant | gelatin | 2.0 g |

There resulted a putty having very good hemostatic and absorbability characteristics.

EXAMPLE 36

| Component 1 | Ca stearate | 3.0 |
|---|---|---|
| Component 2 | tocopheryl acetate | 0.4 |
| Component 2 | acetyl tributyl citrate | 2.3 |
| Absorption Accelerant | gelatin | 2.0 |

The resulting product has characteristics similar to the putty of Example 53.

The foregoing Examples are illustrative of specific embodiments of the present invention. Other embodiments may be prepared by those skilled in the art in accordance with the teachings of the invention.

EXAMPLE 37

| Component 1 | Calcium Stearate | 4 g. |
|---|---|---|
| Component 2 | Pluronic ® L-35* (Molecular Wt. 1900) | 0.2 g |
| Component 12 | Water | 2 g |

*Pluronic 588310, Lot WPAW-502B, BASF, Corp. Mt. Olive, NJ 07828-1234

The ingredients are combined with stirring until a putty-like mass results. The material is easily dispersed in excess water.

The Pluronic in this example was a viscous liquid and formed an excellent putty.

Because this Pluronic is water soluble, it was not necessary to add an absorption accelerant.

EXAMPLE 38

| Component 1 | Calcium Stearate | 2.0 g. |
|---|---|---|
| Component 2 | Tocopheryl acetate | 1.5 g. |
| Component 3 | Pluronic ® F-38* (Molecular Wt. 4700) | 2.0 g. |

*Product 583095, Lot WP1W-515B, BASF Corp., Mt. Olive, NJ 07828-1234

The Pluronic was provided as a "Pastille" and ground to a powder before mixing. The mixture formed an excellent putty.

EXAMPLE 39

| Component 1 | Calcium Stearate | 4.0 g. |
|---|---|---|
| Component 2 | Pluronic ® L-35 (Molecular Wt. 1900) | 3.0 g. |

The Pluronic in this example was a viscous liquid and formed an excellent putty. Because this Pluronic is water soluble, it was not necessary to add an absorption accelerant.

The foregoing Examples are illustrative of specific embodiments of the present invention. Other embodiments, within the scope of the present invention, may be prepared by those skilled in the art as described in the foregoing Specification.

What is claimed is:

1. A body-absorbable, mechanically hemostatic putty composition having no added water and consisting essentially of an intimate admixture of the following Components 1 and 2 and none, or any one or more, of the following Optional Components:
   (1) an absorbable, finely powdered, carboxylic acid salt having a carboxylate anion, and a metallic cation, in intimate admixture with,
   (2) an absorbable composition that is liquid at room temperature comprising a first member that consists of a liquid at room temperature selected from the group consisting of tocopherol, a $C_2$-$C_{10}$ aliphatic monocarboxylic acid ester of tocopherol, a polycarboxylic acid ester of tocopherol, and mixtures thereof, and a second member that is consists of a block copolymer of ethylene oxide and propylene oxide wherein the block copolymer is liquid at room temperature,
   (3) an optional absorbable anti-infective agent, and
   (4) an optional absorbable colorant,
   wherein the amounts of Components 1 and 2 and any Optional Components that may be present are sufficient to form a putty-like consistency at ambient temperature, and wherein Component 2 makes up 10-70% of the composition by weight and the first member makes up 4-5% of the composition by weight.

2. The composition of claim 1 wherein said composition is sterile.

3. The composition of claim 1 wherein the first member of Component 2 consists of a member selected from the group consisting of tocopherol, the acetate, butyrate, caproate, caprylate, caprate and intervening homolog esters thereof, and the citrate or malate esters thereof.

4. The composition of claim 3 wherein the first member of Component 2 consists of tocopherol or tocopheryl acetate.

5. The composition of claim 4 wherein the first member of Component 2 consists of tocopheryl acetate.

6. The composition of claim 1 wherein the carboxylate anion of Component 1 is selected from saturated or unsaturated carboxylic acids containing about 6 to 22 carbon atoms.

7. The composition of claim 6 wherein the carboxylate salt cation of Component 1 is calcium, magnesium, zinc, aluminum, lithium, or barium or mixtures thereof.

8. The composition of claim 7 wherein the carboxylate anion of Component 1 is an aliphatic acid selected from caprylic acid, capric acid, lauric acid, myristic acid, palmitic acid, stearic acid, arachidic acid, and intervening homologs thereof.

9. The composition of claim 8 wherein the carboxylate anion of Component 1 is stearic acid.

10. The composition of claim 8 wherein the carboxylate anion of Component 1 is palmitic acid.

11. The composition of claim 9 wherein the carboxylate salt cation of Component 1 is calcium.

12. The composition of claim 10 wherein the carboxylate salt cation of Component 1 is aluminum.

13. The composition of claim 11 wherein the first member of Component 2 consists of a member selected from-the group consisting of tocopherol, the acetate, butyrate, caproate, caprylate, caprate and intervening homolog esters thereof, and a succinate, citrate or malate ester thereof.

14. The composition of claim 13 wherein the first member of Component 2 consists of tocopheryl acetate.

15. The composition of claim 9 comprising calcium stearate and tocopherol acetate in addition to the block copolymer of ethylene oxide and propylene oxide.

16. The composition of claim 15 comprising anti-infective agent.

17. The composition of claim 1 wherein Component 1 consists of calcium stearate, and the first member of Component 2 consists of tocopheryl acetate.

18. A package comprising the composition of claim 1 wherein said composition is amorphous or in a generally rounded form or in a generally parallelepiped form, wherein said composition is sealed in an aseptic barrier package, and is sterile or sterilizable.

19. The package of claim 18 wherein the package comprises a plunger or applicator whereby said composition is expellable from said package by the application of mechanical pressure applied to the plunger or applicator.

20. The package of claim 18 wherein the package comprises a squeezable, deformable tube having an openable exit port whereby said composition is expellable from said tube by the application of mechanical pressure thereto.

21. The composition of claim 18 wherein said composition is sterile.

22. A method for mechanically controlling the bleeding of bone which comprises applying an effective amount of the composition of claim 1, to the affected area.

* * * * *

UNITED STATES PATENT AND TRADEMARK OFFICE
CERTIFICATE OF CORRECTION

| | | |
|---|---|---|
| PATENT NO. | : 7,989,000 B2 | Page 1 of 1 |
| APPLICATION NO. | : 10/941889 | |
| DATED | : August 2, 2011 | |
| INVENTOR(S) | : Richard L. Kronenthal | |

It is certified that error appears in the above-identified patent and that said Letters Patent is hereby corrected as shown below:

Claim 1, col. 22, line 38, the phrase "ber that is consists of a block copolymer of ethylene", should read: -- ber that consists of a block copolymer of ethylene --

Claim 21, col. 24, line 17, the sentence "The composition of claim 18 wherein said composition", should read: -- The package of claim 18 wherein said composition -- first occurrence of composition Signed and Sealed this
Twenty-seventh Day of September, 2011

David J. Kappos
*Director of the United States Patent and Trademark Office*